US006875616B1

(12) United States Patent
Forssmann et al.

(10) Patent No.: US 6,875,616 B1
(45) Date of Patent: Apr. 5, 2005

(54) PROCESS FOR DETERMINING THE STATUS OF AN ORGANISM BY PEPTIDE MEASUREMENT

(75) Inventors: Wolf-Georg Forssmann, Hannover (DE); Peter Schulz-Knappe, Hannover (DE); Michael Schrader, Hannover (DE); Hans-Georg Opitz, Hannover (DE)

(73) Assignee: BioVision AG (DE)

( * ) Notice: Subject to any disclaimer, the term of this patent is extended or adjusted under 35 U.S.C. 154(b) by 0 days.

(21) Appl. No.: 09/242,254

(22) PCT Filed: Aug. 13, 1997

(86) PCT No.: PCT/EP97/04396

§ 371 (c)(1),
(2), (4) Date: May 7, 1999

(87) PCT Pub. No.: WO98/09036

PCT Pub. Date: Feb. 19, 1998

(30) Foreign Application Priority Data

Aug. 13, 1996 (DE) .......................................... 196 32 521
Jun. 16, 1997 (DE) .......................................... 197 25 362

(51) Int. Cl.$^7$ .......................... G01N 33/48; C12Q 1/68; C12Q 1/70; B01D 59/44

(52) U.S. Cl. ............................. 436/86; 436/63; 436/64; 436/87; 436/173; 436/177; 436/178; 435/5; 435/6

(58) Field of Search ........................ 436/63–64, 86–87, 436/173, 177–178, 518, 6; 435/5–6

(56) References Cited

FOREIGN PATENT DOCUMENTS

| DE | 4427531 | * | 2/1996 |
| JP | 55-37944 | * | 3/1980 |
| WO | 95/02182 | * | 1/1995 |

OTHER PUBLICATIONS

Boos, K. S. et al, Proc. Int. Conf. Biochem. Sep., 2nd (1988), 363–4, editors: Pick, J. et al, Publisher: Hungarian Biochemical Society, Budapest, Hungary.*
J. P. Borel et al, Clinica Chimica Acta 1967, 16, 409–416.*
Klosse et al, Clinica Chimica Acta 1972, 42, 409–422.*
M. Okuda et al, Circulatory Shock 1974, 1, 17–29.*
A. Szymanowicz et al, Ann. Biol. Clin. 1975, 33, 351–358.*
H. W. Leber et al, Verh. Dtsch. Ges. Inn. Med. 1978, 84, 1076–1079.*
W. H. Boesken Current Problems in Clinical Biochemistry 1979, 235–248.*
C. A. White et al, Clinica Chimica Acta 1979, 95, 381–389.*
N. M. K. Ng Ying Kin et al, Analytical Biochemistry 1980, 102, 213–219.*
D. J. Knauer et al, Cancer Research 1980, 40, 4368–4372.*
T. L. Perry et al, Clinica Chimica Acta 1981, 117, 7–12.*
H. Mabuchi et al, Journal of Chromatography 1982, 228, 292–297.*
K. Tellerova et al, Journal of Chromatography 1983, 273, 197–201.*
J. Fareed et al, Seminars in Thrombosis and Hemostasis 1983, 9, 355–379.*
J. H. Johansen et al, Pept., Proc. Eur. Pept. Symp., 17th 1983, 613–616.*
C. Charpentier et al, Clinica Chimica Acta 1984, 138, 299–308.*
N. Koide et al, Acta Med Okayama 1986, 40, 243–248.*
A. M. Cox et al, Journal of Chromatography 1987, 397, 213–222.*
K. S. Boos et al,m Symposia Biologica Hungarica 1988, 37, 87–109.*
S. V. Kharchenko et al, Izv. Akad. Nauk SSSR Ser. Biol. 1988, 524–530.*
T. M. Guman–Wignot et al, Clinical Biochemistry 1989, 22, 377–383.*
H. Kodama et al, Journal of Chromatography 1990, 527, 279–288.*
H. Imamura et al, Journal of Bone and Mineral Research 6, 77–84.*
K. Sugahara et al, Journal of Chromatography 1991, 565, 408–415.*
K. Nagase et al, Nippon Iyo Masu Supekutoru Gakkai Koenshu 1992, 17, 271–274.*
V. Streit et al, Journal of Investigative Dermatology 1995, 105, 562–566.*
T. Nakanishi et al, Journal of the American Society for Mass spectrometry 1995, 6, 854–859.*
J. Turkova et al, Journal of Molecular Recognition 1996, 9, 360–363.*
R. Wang et al, Jouornal of Biological Chemistry 1996, 271, 31894–31902.*
T. Krishnamurthy et al, Journal of Natural Toxins 1997, 6, 121–162.*
M. Schrader et al, Journal of Chromatography A1997, 776, 139–145.*
Harry et al; Antigen Detection for Human Immunodeficiency Virus; Clinical Microbiology; Vol, 2, pp. 241–249.*
Ausbel et al; Short Protocols in Molecular Biology; pp. 10–55to 10–58 and 10–64 to 10–69.*
Jimenez et al; Neuropeptide Expression and Processing as Revealed by Direct Matrix–Assisted Laser Desorption Ionization Mass Spectrometry of Single Neurons; Journal of Neurochemistry; Vol, 62; pp. 404–407.*

*Primary Examiner*—Arlen Soderquist
(74) *Attorney, Agent, or Firm*—Olson & Hierl, Ltd.

(57) ABSTRACT

A method for detecting the condition of an organism through the measurement of peptides from a sample of said organism containing high- and low-molecular weight peptides, as an indication of the condition of said organism, wherein
low-molecular weight peptides are directly detected and characterized; and
related to a reference.

23 Claims, No Drawings

OTHER PUBLICATIONS

A. Hernanz et al "Gastrointestinal Peptide Profile in Children with Celiac Disease" Journal of Pediatric Gastroenterology, vol. 6, No. 3, 1987, New York, NY, pp. 341–345, XPOO2050736.

M. J. Staquet et al "Keratin polypetide profile in psoriatic epidermis normalized by treatment with etretinate". Archives of Dermatological Research, vol. 275, No. 2, 1983, Berlin, Germany, pp. 124–129, XPOO2050737.

C.R. Jimenez et al "Pattern changes of pituitary peptides in rat . . . " Proceedings of the National Academy of Sciences, USA, vol. 94, No. 17, 1997, Bethesda, MD, pp. 9481–9486, XP002050738.

* cited by examiner

PROCESS FOR DETERMINING THE STATUS OF AN ORGANISM BY PEPTIDE MEASUREMENT

This application is the National Stage of PCT/EP97/04396, filed Aug. 13, 1997.

BACKGROUND OF THE INVENTION

1. Field of the Invention

The present invention relates to a method for detecting the condition of an organism through the measurement of peptides from a sample of said organism.

2. The Prior Art

Various analytical methods are employed for detecting the condition of an organism. Thus, for example, in the diagnostics of higher organisms, when pathological results are obtained, attempts are made to fathom the causes of the pathological change on the basis of the symptoms in order to develop a causal therapy. Further, efforts are being made to develop a reference of an average "healthy" organism by sequencing the genomes of organisms and establishing "wild type genomes" in order to be able to discover individual deviations which could indicate possible pathogenic developments by performing corresponding gene analyses. A drawback of the first methodological approach is that diagnostics free from hypotheses (bias-free) cannot be performed since the diagnostics therein are already based on assumptions. A drawback of the second method is that it will not be possible for a long time to diagnose the important or even all diseases attributed to genetic dysfunctions. Another drawback of the latter method may also be that a mutation on a gene does not necessarily result in expression of the related phenotype.

Thus, it would be desirable to provide a universally employable diagnostic method by which it is possible to avoid the drawbacks mentioned and, in particular, to perform diagnostics free from hypotheses. In addition, the diagnostic method should be universally employable, not be restricted to higher developed systems, but also be employable for detecting the condition of lower organisms. In addition, it should be easy to establish and capable of being carried out with per se known techniques.

SUMMARY OF THE INVENTION

Thus, it has been the object of the present invention to provide such a method.

Surprisingly, the object of the invention is achieved in a simple manner by a method with the features according to the invention.

The method according to the invention for detecting the condition of an organism starts by taking a sample from the organism to be examined. This sample may also be the complete organism. The sample must contain low-molecular weight peptides, but there is no interference from high-molecular weight peptides or proteins which are also contained in the sample in addition to low-molecular weight peptides. According to the invention, the low-molecular weight peptides are directly detected and characterized and serve as indicators of the condition of the organism. It is possible to detect single peptides directly by a measuring technique, to detect several peptides by a measuring technique, or even all the low-molecular weight peptides present in the sample which can be detected by a measuring technique. Unlike conventional analytical or diagnostic methods, such as gel electrophoresis or two-dimensional electrophoresis and, for example, clinical diagnostic methods, the method according to the invention does not examine the high-molecular weight structures, such as proteins. As opposed to per se known diagnostic methods, such as radioimmunoassay or other competitive assays for the measurement of peptide hormones and the like, the low-molecular weight peptides are directly detected according to the invention by some measuring technique rather than indirectly as in the methods mentioned. The distribution of low-molecular weight peptides in a representative cross-section of defined controls is used as a reference.

In the method according to the invention, the sample to be examined may be derived from tissue or fluid samples from the organism the condition of which is to be detected, or it may be the organism itself or parts thereof. When lower organisms are examined, the organism itself is preferably used as the sample. Such lower organisms include, in particular, single-celled organisms, such as procaryotic systems or simple eucaryotic systems, such as yeasts or other microorganisms.

According to the invention, the low-molecular peptides employed for measurement shall preferably have a molecular weight of not more than 30,000 Dalton. The lower limit is not actually critical, but dipeptides represent the lower limit of low-molecular weight peptides to be detected according to the invention. Particularly preferred are molecular weights of the low-molecular weight peptides of from 100 to 10,000 Dalton.

If required, for example, due to a changed measuring arrangement, it may be advantageous to remove high-molecular weight peptides or proteins and other biopolymers which might interfere with the measurement from the sample. This is not required, in particular, in cases where the higher-molecular weight peptide compounds are not covered by the measuring method to be employed according to the invention.

Preferably, according to the invention, mass spectroscopy is employed for detecting the low-molecular weight peptides. Particularly preferred is the so-called MALDI method (matrix assisted laser desorption ionization mass spectroscopy). If mass spectroscopy is employed as a method, it is recommendable to employ the data obtainable by said mass spectroscopy for characterizing the low-molecular weight peptides, such as their molecular weights. It is also possible, under particular circumstances, to analyze other parameters, such as the charge of the peptides, or the characteristic retention times on chromatographic columns, or a fragment pattern of the low-molecular weight peptides, or combinations of the mass and charge of the low-molecular weight peptides.

Depending on the additional questions connected with the detection of the condition of the organism, it may be advantageous to divide the sample into several fractions and to analyze the samples under different aspects or with different measuring arrangements, and thus to detect a condition of the organism.

The organisms include, in particular, procaryotes, eucaryotes, multicellular organisms, cells from tissue cultures, cells from animals and humans. Thus, it becomes possible according to the invention to examine the condition of genetically engineered or transformed and/or conditioned organisms. This may be advantageous, in particular, for checking transformed systems in order to recognize any unexpected or undesirable properties which might have been developed by transformed organisms, for instance, by forming peptides indicative of undesirable or unexpected properties, such as toxic properties.

In particular, any deliberately or unintentionally performed manipulation (conditioning) of an organism may influence its condition, whether during the administration of medicaments, gene therapy, infections, in the working place from contact with chemical substances, in test animals, especially transgenic animals and knock-out mutants. Especially in the case of such methods, an intra- and interindividual comparison, for example, through the chronological taking of samples from an organism prior to and in the course of one of the above mentioned measures, or a comparison with untreated control organism may be used to check whether the predicted and desired changes in condition have actually occurred, and whether, in addition or instead, unpredicted, undesirable or desirable, changes have occurred which are detected by the method according to the invention without the need to recur to hypotheses.

Therefore, the method according to the invention is also useful, for example, for accompanying clinical studies, toxicological examinations in the testing of medicaments of all kinds, for analyzing/detecting decomposition products, for the identification of gene products.

In veterinary and human medicine, the method according to the invention gains its outstanding importance by the fact that it enables the detection of the condition of the respective organism without the need to recur to hypotheses. Thus, rather than performing a confirmation assay based upon a preconceived opinion, a real overall picture of the condition of the organism examined can be created. The method according to the invention, which may be designated as a differential peptide display, is based on the fact that a particular peptide pattern is present in a healthy organism which is therefore capable of serving as a reference standard. Now, if the peptide condition of an individual is recorded and compared to that of the reference, deviations can be detected which provide a first indication of a possibly pathogenic condition. By detecting the deviations established by comparison with similar pathogenic conditions from corresponding samples of a diseased, it is then possible to identify the respective disease directly from the analysis by a mere comparison of the deviations in the peptide pattern of the sample of said individual, and correspondence of the deviation with an assigned clinical picture.

According to the invention, one may proceed as follows, in particular. Ultrafiltrates from body fluids and tissue extracts may first be used for preparing a reference sample. Recovery of the filtrate peptides and their separation into fractions is performed, for example, by collecting low-molecular weight peptide fractions. The characterization of the peptide fractions may be effected, for example, by their retention behavior and molecular weight, which can be determined by chromatography or mass spectroscopy. For example, if an ultrafiltrate from patients suffering from a known disease is used and compared with the previously established spectrum of healthy reference subjects, the deviating pattern enables an assignment of the specific disease to the condition of the respective peptide mixture. Thus, this method may also be employed in a per se conventional manner, for example, by immediately interrogating the appropriate peptide pattern indicative of pathogenic changes. In some cases, this may even be one peptide characteristic of the respective disease. For example, if a sample is analyzed from a patient for whom a particular clinical picture can be recognized and a hypothesis for the cause of such disease exists, this specific peptide may also be interrogated in the analysis according to the invention, and if the result is positive, appropriate therapeutic schemes may be established. Thus, it is altogether possible to first take a sample from the patient, to record a condition by the method according to the invention, and then, if the presence of a deviation indicative of pathogenic conditions is established, either to perform a control measurement by per se known confirmation assays recurring to the usual clinical assays, or to perform such control measurement by specifically screening for the indicator of the pathogenic condition.

Peptides may be recovered by methods known to those skilled in the art, such as ultrafiltration of the respective starting material. When doing so, filters are used having a molecular exclusion size within the range claimed according to the invention, i.e., between that of a dipeptide and a maximum of 30,000 Dalton. By appropriately selecting the respective membranes, it is also possible to obtain fractions of particular molecular weights. Preferably, from 0.2 ml to 50 l of filtrate is obtained from the filtration, which is adjusted, for example, to a pH value of from 2 to 4 by acidification with diluted hydrochlorid acid immediately after the end of the filtration. The amounts mentioned especially serve to examine pooled samples, for developing reference samples from healthy subjects, or for determining disease-specific peptide markers for establishing a peptide data base.

The peptides present in the filtrate after ultrafiltration are recovered by adsorption to chromatographic materials, especially cation exchangers, such as Fractogel, anion exchangers-Fractogel TMAE, and reversed phase (RP) materials, followed by elution with linear gradients or step gradients. For further purification, other chromatographic separations, especially through reversed phase materials, may optionally be effected.

The measurement of the peptide fractions is preferably performed by mass-spectrometrical analysis, especially with MALDI MS (matrix assisted laser desorption ionization mass spectrometry) or ESI MS (electrospray ionization MS). These are methods which can be used for the analysis of peptides. This preferably involves the on-line coupling of Microbore reversed phase separation and mass spectrometry (LC-MS coupling). From the data obtained, a multidimensional table is established based on retention behavior, molecular weight and signal intensity as the preferred guiding parameters. However, other quantities which can be determined with the mentioned methods may also be recorded.

The data about patients with a known basic disease obtained from the above mentioned steps are compared to the similarly obtained data from a healthy reference population. Both qualitative changes (e.g., the occurrence of new peptides or the lacking of peptides) and quantitative changes (the increased or decreased occurrence of individual peptides) are detected. If required, the targets defined by the comparative analysis may further be purified and identified by methods of peptide chemistry known to those skilled in the art. The sequence information obtained can then be compared with protein and nucleic acid data bases and subsequently with data from the literature. The relevance of the represented peptides with respect to the examined disease is checked by functional studies and by screenings with appropriate groups of patients.

DETAILED DESCRIPTION OF PREFERRED EMBODIMENTS

EXAMPLE 1

Use of Body Fluids: Blood Filtrate (Hemofiltrate, HF)

1. Recovery of HF

HF is recovered by arterio-venous or veno-venous hemofiltration performed by techniques known to those skilled in the art with selected patients or subjects. The recovery of HF is effected in the same way, in principle, as performed as a matter of a routine in patients with chronical renal disease. Through an arterial drain and venous feed (arterio-venous hemofiltration) or venous drain and venous feed (veno-venous hemofiltration), the patient's blood is passed with the aid of a hemofiltration device (e.g., Hemoprozessor, Sartorius, Göttingen; AK 10 HFM, Gambro, Hechingen)

through a hemofilter (e.g., Hemoflow F 60 or Hemoflow HF 80 S, Fresenius, Bad Homburg; Hemoflow FH 77 H and Hemoflow HF 88 H, Gambro) which has a molecular exclusion size of up to 30 kDa. The filtrate volume withdrawn from the patient is substituted by an electrolyte solution (e.g., SH 01, SH 05, SH 22, SH 29, Schiwa, Glandorf).

According to the present method, a diagnostic hemofiltration is performed with the aim to obtain from 1 to 30 l of HF from a patient in the course of one hemofiltration. For avoiding proteolysis, the hemofiltrate is immediately adjusted to a pH value between 2 and 4 with diluted acid (e.g., 1 M HCl), and cooled to 4° C.

2. Recovery of the HF Peptides and Separation Into Fractions 2.1 Peptide Extraction with Stepwise Elution 10 l of hemofiltrate is diluted with deionized water to provide a conductivity of 6 mS/cm, and its pH value is adjusted to 2.7 with hydrochlorid acid. The HF is then applied to a chromatographic column. After binding of the HF peptides, the bound peptides are eluted with a pH step elution using 7 buffers with increasing pH values.

Chromatographic conditions:
flow for application: 100 ml/min
flow for elution: 30 ml/min
detection: 214, 280 nm
column: Vantage (Amicon, Witten), 6 cm diameter×7 cm filling height
column material: Fraktogel TSK SP 650 M (Merck, Darmstadt)
equipment: BioCAD 250, Perseptive Biosystems, Wiesbaden-Nordenstadt

| buffer | pH value | buffer substances | molarity |
| --- | --- | --- | --- |
| elution buffer 1 | 3.6 | citric acid. | 0.1 |
| elution buffer 2 | 4.5 | acetic acid | 0.1 |
| elution buffer 3 | 5.0 | malic acid | 0.1 |
| elution buffer 4 | 5.6 | succinic acid | 0.1 |
| elution buffer 5 | 6.6 | sodium dihydrogenphosphate | 0.1 |
| elution buffer 6 | 7.4 | disodium hydrogenphosphate | 0.1 |
| elution buffer 7 | 9.0 | ammonium carbonate | 0.1 |

Eluates 1–7 are separately collected.

2.2 Second Chromatographic Separation

Eluates 1–7 are separately subjected to chromatography through a reversed phase column.

Chromatographic conditions:
flow for application: 10 ml/min
flow for elution: 4 ml/min
detection: 214 nm
column: HPLC steel column, 1 cm diameter, 12.5 filling height
column material: Source RPC 15 μm (Pharmacia, Freiburg)
equipment: BioCAD, Perseptive Biosystems, Wiesbaden-Nordenstadt
The eluate is collected in 4 ml fractions.

3. Mapping of the Peptide Fractions.

3.1

Aliquots of the fractions obtained in 2.2 are applied to a Microbore reversed phase column and eluted in a gradient. Detection is effected with a UV detector and on-line with an electrospray mass spectrometer.

Chromatographic conditions:
flow for application: 20 μl/min
flow for elution: 20 μl/min
detection: 220 nm
column: C18 AQS, 3 μm, 120 A, 1 mm diameter, 10 cm length (YMC, Schermbeck)
equipment: ABI 140 B Dual Solvent Delivery System
buffer A: 0.06% trifluoroacetic acid in water
buffer B: 80% acetonitrile in A
gradient: 0% B to 100% B in 90 min
On-line mass spectrometry:
API III with electrospray interface (Perkin-Elmer, Weiterstadt) positive ion mode
measuring range:m/z from 300 to 2390
scan time: 7 s
scan window: 0.25 m/z Data acquisition is performed with MacSpec or MultiView Soft-ware (Perkin-Elmer).

3.2 MALDI MS Measurement of the Individual Fractions

Aliquots of the fractions obtained in 2.2 are measured with different matrix substances, e.g., with the addition of L-(−)-fucose, in MALDI MS.

From the raw data, a multidimensional table is established considering the scan number, signal intensity and, after calculation, of the masses from the multiple-charged ions of a scan.

4. Comparative Analysis 4.1 Identification of Novel or Lacking Peptides or Those Significantly Deviating in Quantity By comparing the data sets obtained under 3.3, which may also be referred to as peptide maps, qualitative and/or quantitative differences are established. Considering controls and samples, individual data sets or sets of data sets are used for comparison.

4.2 Peptide-chemical Characterization of the Identified Targets

From the raw material obtained (e.g., large preparations of hemofiltrate), the identified targets are purified in such amounts as allow identification, using the different chromatographic separation techniques known to those skilled in the art which are generally employed for separating peptide mixtures (reversed phase, ion-exchange, size exclusion, hydrophobic interaction, etc.). After each chromatographic separation of a fraction, the targets are again identified in the fractions by ESI MS, MALDI MS or LC MS. This procedure is repeated, with variation of the chromatographic parameters, until a pure product of the desired specification, i.e., retention time and molecular weight, has been obtained. This is followed by the determination of a partial or complete amino acid sequence or a fragment pattern. Subsequently, a data base comparison is performed with the known data bases (Swiss-Prot and EMBL-Peptid- und Nucleinsäure-Datenbank), with the object to identify the partial or complete sequence or a fragment pattern. If no data base entry exists, the primary structure is clarified.

EXAMPLE 2

Use of Body Fluids: Ascitic Fluid

1. Recovery of Ascitic Fluid

Ascitic fluid is formed as an extravascular exsudate in various diseases (malignant tumors, liver disorders etc.). According to the present method, between 10 ml and 10 l of ascitic fluid is obtained by punction and then immediately adjusted to a pH value of between 2.0 and .4.0 with: diluted acid (e.g., 1 M HCl) in order to avoid proteolysis, and cooled to 4° C. After ultrafiltration over a cellulose triacetate membrane with an exclusion size of 30 kDa (Sartocon mini-apparatus, Sartorius), the filtrate is further used as a source of peptides.

2. Recovery of the Ascitic Fluid Peptides and Separation into Fractions 2.1 Peptide Extraction with Gradient Elution 5 of ascitic fluid filtrate is adjusted to pH 2.0 and separated through a preparative reversed phase column.

Chromatographic conditions:
flow for application: 40 ml/min
flow for elution: 40 ml/min
detection: 214 nm, 280 nm
column: Waters cartridge system, 4.7 cm diameter, 30 cm filling height
column material: Vydac RP-C18, 15–20 µm
equipment: BioCAD, Perseptive Biosystems, Wiesbaden-Nordenstadt
buffer A: 0.1% trifluoroacetic acid in water
buffer B: 80% acetonitrile in A
gradient: 0% B to 100% B in 3000 ml
The eluate is collected in 50 ml fractions.
The further course of the characterization corresponds to that in Example 1.

EXAMPLE 3

Use of Body Fluids: Urine

1. Recovery of Urine

Urine is directly recovered as catheter urine or spontaneous urine from patients in amounts of from 0.5 to 50 1 and immediately adjusted to a pH value of between 2.0 and 4.0 with diluted acid (e.g., 1 M HCl) in order to avoid proteolysis, and cooled to 4° C. After ultrafiltration over a cellulose triacetate membrane with an exclusion size of 30 kDa (Sartocon mini-apparatus, Sartorius), the filtrate is further used as a source of peptides.

2. Recovery of the Urine Peptides and Separation into Fractions 2.1 Peptide Extraction with Stepwise Elution 10 1 of urine filtrate is diluted with water to provide a conductivity of 6 mS/cm, and its pH value is adjusted to 2.7 with HCl. The urine filtrate is then applied to a chromatographic column. After binding of the peptides, the bound peptides are eluted with a saline gradient.

Chromatographic conditions:
flow for application: 100 ml/min
flow for elution: 30 ml/min
detection: 214 nm
column: Vantage (Amicon, Witten), 6 cm diameter×7 cm filling height
column material: Merck Fraktogel TSK SP 650 M
equipment: BioCAD 250, Perseptive Biosystems, Wiesbaden-Nordenstadt
buffer A: 50 mM $NaH_2PO_4$, pH 3.0
buffer B: 1.5 M NaCl in A
gradient: 0% B to 100% B in 2000 ml
The eluate is collected in 10 pools of 200 ml each.

2.2 Second Chromatographic Separation

The fractions are separately subjected to chromatography through a reversed phase column.

Chromatographic conditions:
flow for application: 10 ml/min
flow for elution: 4 ml/min
detection: 214 nm
column: HPLC steel column, 1 cm diameter, 12.5 cm filling height
column material: Pharmacia Source RPC 15 µm
equipment: BioCAD, Perseptive Biosystems, Wiesbaden-Nordenstadt
buffer A: 0.1% trifluoroacetic acid in water
buffer B: 80% acetonitrile in A
gradient: 0% B to 100% B in 200 ml
The eluate is collected in 4 ml fractions.
The further course of the characterization corresponds to that in Example 1.

What is claimed:

1. A method for detecting a pathogenic conditions in an organism comprising the steps of:
    measuring all low-molecular weight peptides having a molecular weight of not more than 30,000 Daltons detectable by MALDI mass spectrometry present in a sample of body fluid taken from said organism
    by directly detecting said low-molecular weight peptides by MALDI mass spectrometry; to provide a distribution of low-molecular weight peptides; and
    relating said low-molecular weight peptides to a reference comprising a distribution of low-molecular weight peptides in a representative cross-section of defined controls of said organism to produce a differential peptide display;
    wherein said body fluid sample is selected from the group consisting of a hemofiltrate, an ascitic fluid, and urine, wherein said organism is an animal or a human, and wherein said differential peptide display is indicative of a pathogenic condition.

2. The method according to claim 1, wherein said detected low-molecular weight peptides have a molecular weight of from 100 to 10,000 Daltons.

3. The method according to claim 1, wherein high-molecular weight peptides having a molecular weight of greater than 30,000 Daltons are also present in said sample and said high-molecular weight peptides are either separated off prior to measurement of said low-molecular weight peptides, or left unconsidered, in terms of measurement or evaluation, in the recording of the sample.

4. The method according to claim 1, wherein said sample is divided into different fractions prior to said measurement of the low-molecular weight peptides, and the fractions are measured under different detection conditions.

5. A method of detecting the physiological condition of an organism without reference to a preconceived diagnosis comprising the steps of:
    (a) directly measuring the distribution of all detectable low-molecular weight peptides in a sample from a test organism; and
    (b) comparing the distribution measured in step (a) to a distribution of low-molecular weight peptides from a sample of a reference organism to provide a differential peptide display illustrating the differences in low-molecular weight peptide distribution between the test organism and the reference organism;
    wherein the low-molecular weight peptides measured have a molecular weight of not more than 30,000 Daltons; said distributions of low-molecular weight peptides are directly measured by mass spectrometry; and wherein the differential peptide display provides for detection of the physiological condition of the test organism without reference to a preconceived diagnostic hypothesis regarding the condition of the test organism.

6. The method of claim 5 wherein the distributions of low-molecular weight peptides are measured by MALDI mass spectrometry or electrospray ionization mass spectrometry.

7. The method of claim 5 wherein the samples are separated into fractions by liquid chromatography prior to measuring the low-molecular weight peptide distributions.

8. The method of claim 5 wherein the low-molecular weight peptides measured have a molecular weight of from 100 to 10,000 Daltons.

9. The method of claim 5 wherein the test organism and reference organism are both humans or are both the same species of animal.

10. The method of claim 9 wherein the reference organism is a normal, healthy organism, and wherein the differential peptide display indicates whether the test organism has a physiological condition that differs from the physiological condition of the healthy reference organism.

11. The method of claim 10 wherein the differential peptide display is compared to differential peptide displays from organisms with known pathological conditions in order to diagnose whether the test organism has a known pathological condition.

12. The method of claim 5 wherein the samples are ultrafiltrates of a bodily fluid from the organism selected from the group consisting of a hemofiltrate, a urine ultrafiltrate, and an ascitic fluid ultrafiltrate.

13. The method of claim 12 wherein the ultrafiltrate is obtained by filtering the bodily fluid through a size exclusion membrane having an exclusion size of 30,000 Daltons.

14. The method of claim 5 wherein the sample of the reference organism is from the same individual test organism and the differential peptide display indicates a physiological change in the test organism over a period of time.

15. The method of claim 5 wherein the test organism is a genetically engineered organism and the reference organism is a genetic control organism; and wherein the differential peptide display indicates whether the genetically engineered organism exhibits an unpredicted, undesirable or desirable physiological change relative to the genetic control reference organism.

16. The method of claim 5 wherein high-molecular weight peptides are also present in said sample and said high-molecular weight peptides are either separated off prior to measurement of said low-molecular weight peptides, or left unconsidered, in terms of measurement or evaluation, in the recording of the sample.

17. A method of detecting a pathological condition in a human or animal without reference to a preconceived diagnosis comprising the steps of:

(a) directly measuring the distribution of all detectable low-molecular weight peptides in a sample from a test organism;

(b) comparing the distribution measured in step (a) to a distribution of low-molecular weight peptides from a sample of a reference organism to provide a differential peptide display illustrating the differences in low-molecular weight peptide distribution between the test organism and the reference organism; and (c) comparing the differential peptide display in step (b) with a differential peptide display from an organism having a known pathological condition;

wherein each of the test organism, the reference organism, and the organism having a known pathological condition is a human or each is an animal; the low-molecular weight peptides measured have a molecular weight of not more than 30,000 Daltons; said distributions of low-molecular weight peptides are directly measured by mass spectrometry; and wherein the comparison in step (c) provides for diagnosis of a pathological condition in the test organism without reference to a preconceived diagnostic hypothesis regarding the condition of the test organism.

18. The method of claim 17, wherein the low-molecular weight peptides measured have a molecular weight of from 100 to 10,000 Daltons.

19. The method of claim 17 wherein the samples are separated into fractions by liquid chromatography prior to measuring the low-molecular weight peptide distributions.

20. The method of claim 17 wherein the samples are ultrafiltrates of a bodily fluid from the organism selected from the group consisting of a hemofiltrate, a urine ultrafiltrate, and an ascitic fluid ultrafiltrate.

21. The method of claim 20 wherein the ultrafiltrate is obtained by filtering the bodily fluid through a size exclusion membrane having an exclusion size of 30,000 Daltons.

22. The method of claim 17 wherein the distributions of low molecular weight peptides are measured by MALDI or electrospray ionization mass spectrometry.

23. The method of claim 17 wherein high-molecular weight peptides are also present in said sample and said high-molecular weight peptides are either separated off prior to measurement of said low-molecular weight peptides, or left unconsidered, in terms of measurement or evalution, in the recording of the sample.

* * * * *

UNITED STATES PATENT AND TRADEMARK OFFICE
CERTIFICATE OF CORRECTION

PATENT NO. : 6,875,616 B1
DATED : April 5, 2005
INVENTOR(S) : Forssmann et al.

Page 1 of 1

It is certified that error appears in the above-identified patent and that said Letters Patent is hereby corrected as shown below:

Column 6,
Line 62, change "a pH value of between 2.0 and .4.0 with:" to -- a pH value of between 2.0 and 4.0 with --.

Column 7,
Line 4, change "5 of ascitic" to -- 5 1 of ascitic --.

Signed and Sealed this

Fifteenth Day of November, 2005

JON W. DUDAS
*Director of the United States Patent and Trademark Office*